United States Patent [19]
Swartz et al.

[11] Patent Number: 6,039,046
[45] Date of Patent: Mar. 21, 2000

[54] SINGLE-USE ORAL PROTECTOR ESPECIALLY FOR USE IN ELECTROCONVULSIVE THERAPY

[75] Inventors: Conrad Melton Swartz, Richmond Heights, Mo.; Richard Stephen Abrams, Chicago, Ill.

[73] Assignee: Somatics, Inc., Lake Bluff, Ill.

[21] Appl. No.: 09/290,102

[22] Filed: Jan. 12, 1999

[51] Int. Cl.[7] .................................................. A61C 5/14
[52] U.S. Cl. .......................................... 128/859; 128/861
[58] Field of Search .................................. 128/846, 848, 128/859–862, 206.24, 207.14

[56] References Cited

U.S. PATENT DOCUMENTS

| | | | |
|---|---|---|---|
| 2,694,397 | 11/1954 | Herms | 128/861 |
| 4,222,378 | 9/1980 | Mahoney | 128/206.24 |
| 4,867,147 | 9/1989 | Davis | 128/859 |
| 5,235,991 | 8/1993 | Minneman | 128/859 |
| 5,469,865 | 11/1995 | Minneman | 128/859 |

*Primary Examiner*—Michael A. Brown
*Attorney, Agent, or Firm*—Eliot S. Gerber

[57] ABSTRACT

An oral protector, especially for use by patients during electroconvulsive therapy (ECT) consists of a flat unitary member which is preferably stamped from a flat sheet of material. The protector is elastic and formed of a closed-cell material, such as polyurethane plastic resin or artificial rubber. It has an elongated, generally elliptical shaped central opening which acts as an air passage.

13 Claims, 2 Drawing Sheets

SINGLE-USE ORAL PROTECTOR ESPECIALLY FOR USE IN ELECTROCONVULSIVE THERAPY

FIELD OF THE INVENTION

The present invention relates to medical devices and more particularly to a medical mouthpiece for protecting the teeth, tongue, gums, buccal (cheek) mucosa, and lips from biting injury during the administration of electroconvulsive therapy (ECT).

BACKGROUND OF THE INVENTION

The related art discusses various devices used, and suggested in the past for protecting the teeth, tongue, and lips from biting injury during the administration of electroconvulsive therapy. One device, called an "Oberto" cushion, is shown in U.S. Pat. No. 2,521,084. It uses an oral protector made of soft rubber. It is sterilizable and re-usable, which presents various problems, discussed below. The Oberto mouthpiece has a rear biting portion that fits between the teeth, an anterior rim that fits between the teeth and the lips, and a more anterior hollow tube that transmits air or oxygen into the oral cavity and thence to the lungs.

Another mouthpiece, of the type shown in U.S. Pat. No. 5,235,991, is called "PROMAX." That patent is to Dr. Susan Minneman. The "PROMAX" device is a mouthpiece constructed from cardboard and foam. The "PROMAX" is a single-use disposable mouthpiece. It positions cushioning foam only between the molars so if a molar is loose or missing, the uncushioned anterior teeth must bear the load of the bite. In addition, there is no air channel as its thin cardboard anterior portion does not provide any separation of the lips. A third device is called the "BITE-BLOC" and relates to U.S. Pat. No. 4,112,939 of Paul Blachly. That mouthpiece is made from a plastic-like material much harder than rubber. In some cases the Blachly "BITE-BLOC" does not cover even the patient's second molars. That device is made of a hard material which can increase the risk of tooth fracture. A fourth device, which it is believed is not yet marketed (Dr. C. Kellner and Medical U. of South Carolina) uses styrofoam to make a single-use (disposable) mouthprop. The Kellner mouthprop does not have an air channel and may obstruct the flow of air. When used with some commonly used oxygen masks, its anterior portion may extend too far forward and prevent an air-tight seal with the mask.

The prior devices have the following drawbacks:
1. During ECT the jaw muscles contract powerfully, clamping the teeth together with great force. Unless sufficient compressible material is interposed between the teeth, especially between the upper and lower molars during this clamping movement, excess pressure is placed on the weaker incisors, leading to possible tooth fracture. Even if sufficiently compressible material is initially correctly interposed between the molars, unless the mouthpiece oral protector is dimensionally stable, the clamping action of the jaw can laterally displace the protector in either the lingual (tongue's) or buccal (cheek's) direction. That type of slippage can reduce or eliminate the protective effect on the incisors.
2. Unless the mouthpiece oral protector is made from a sufficiently dense and malleable material, the powerful biting action during ECT can dislodge or break off small pieces of the protector. Those pieces may be aspirated, leading to pneumonia and other pulmonary complications.
3. During ECT the brain, heart, and other vital organs require an increased supply of oxygen. Unless the oral protector design permits full and easy flow of oxygen into the oral cavity, and then to the lungs, adverse tissue effects of reduced oxygen availability can occur, including cardiac arrhythmias and brain dysfunction. Moreover, because an oxygen mask is used to deliver oxygen during ECT, the oral protector must not extend so far anteriorly as to block correct positioning of the oxygen mask.
4. Some of the prior mouthpieces are not single-use disposable devices but are intended to be sterilized and re-used. Reusable medical products have transmitted a variety of infectious pathogens between patients. Incomplete decontamination and disinfection are the main causes. Such decontamination is especially a problem with non-metal devices such as mouthpieces. The care of such cross-infections is usually not reimbursed by medical insurance plans. Generally, reusable mouthpieces are disfavored since it is costly to wash, transport, sterilize, and wrap them after each use. In addition, it is necessary to create and maintain records on each re-use, which is a time-consuming burden.

Thus, the key elements of a medically suitable mouthpiece oral protector are as follows:
a. Coverage of all teeth
b. Compressibility
c. Air channel
d. Structural stability
e. Compositional integrity
f. Single use
g. Dimensions compatible with oxygen mask In view of these key elements, it is seen that the presently commercially available ECT mouthpieces are deficient in one or more respects.

The "OBERTO" reusable model has a tubular air channel which projects far enough anteriorly to occasionally block correct application of the oxygen face mask. This causes the air channel to bend and collapse, defeating its purpose. It is subject to incomplete disinfection/contamination and therefore the possibility of transmitting cross-infections.

The "PROMAX" single-use model lacks sufficient compressible material to protect all teeth. It can be hazardous in the presence of loose or missing teeth. It lacks an air channel, and the presence of only a very thin cardboard surface between the lips can allow the lips to compress anteriorly, blocking the flow of oxygen.

The "BLACHLY BITE-BLOC" reusable model has biting surfaces which extend insufficiently rearward to protect the rearmost (3d) molars in all cases. It is composed of a too-rigid, non-compressible material that can cause tooth damage during the powerful initial biting action during ECT. It also may not be completely disinfected after use, resulting in the possibility of cross-infections.

The "KELLNER MOUTHPROP" is constructed of styrofoam and thus subject to partial disintegration during the shearing force created by the biting action of ECT, raising the risk of aspiration pneumonia. It lacks rear structural stability, raising the possibility of lingual or buccal slippage during biting and loss of the protective function. It lacks a specific air channel. In addition, it extends far enough anteriorly to compromise oxygen mask fit in some patients.

SUMMARY OF THE INVENTION

The present invention comprises a one-piece, unitary structurally stable, single-use, oral protector made of a compressible elastic material. It features a two-dimensional geometry. Consequently, it may be stamped, using a stamping die, from a flat sheet of suitably compressible material. It is therefore less expensive to manufacture than mouthpieces requiring injection molds for their production. The mouthpiece covers all the teeth and has an integral air channel. It has a softly rounded anterior aspect that does not extend far enough to compromise the fit of any presently manufactured oxygen mask.

Preferably the oral protector is made of a suitable closed-cell plastic resin foam. One preferred closed-cell foam is polyurethane foam and another is neoprene (closed-cell foam artificial rubber). The use of such closed-cell foam provides a suitable elasticity, e.g., the material rebounds in shape after being compressed. The closed-cell material has a suitable compressability, e.g., the material will not injure the patient's teeth and jaw due to its hardness. Alternatively to closed-cell foam, the material of the oral protector may be a suitable natural or artificial rubber. In all cases, the selected material preferably has the following properties: (i) a smooth outer surface, (ii) a spring-like mass due to the closed-cell matrix, and (iii) it is available in different densities.

Preferably the oral protector is made in two sizes—a smaller size, generally for female patients, and a larger size, generally for male patients.

BRIEF DESCRIPTION OF THE DRAWINGS

The inventors' presently known best mode of practicing the present invention is set forth in the following detailed description of the invention, which should be considered in conjunction with the accompanying drawings.

In the drawings.

DETAILED DESCRIPTION OF THE INVENTION

The oral protector of the present invention is especially adapted for use in electroconvulsive therapy (ECT). However, it may be useful for other situations, including as a training device for lessening bruxism (grinding of teeth) and to facilitate the free flow of air into the oropharynx, and thence to the lungs, in individuals suffering from sleep apnea.

In addition to its use in ECT, the oral protector may be used during other medical procedures such as cardioversion/defibrillation. It may also be used during surgical and anesthesia procedures which require oral protection or there is a risk of spontaneous seizure, for example, during a neurosurgical operation. The dimensions of the oral protector of FIGS. 1–4 were derived from a study of dental impressions in a sample of 35 men and women. Based on that sample group, the size will fit more than 95% of all adult patients.

Figure 1:
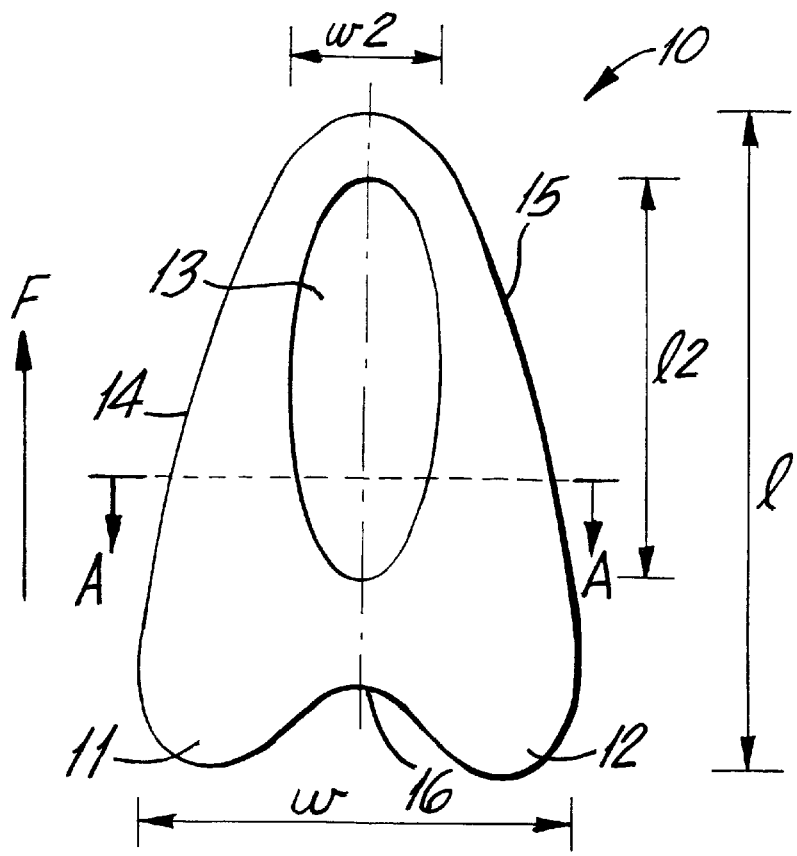
FIG. 1 is a top plan view of the oral protector of the present invention.
Figure 2:
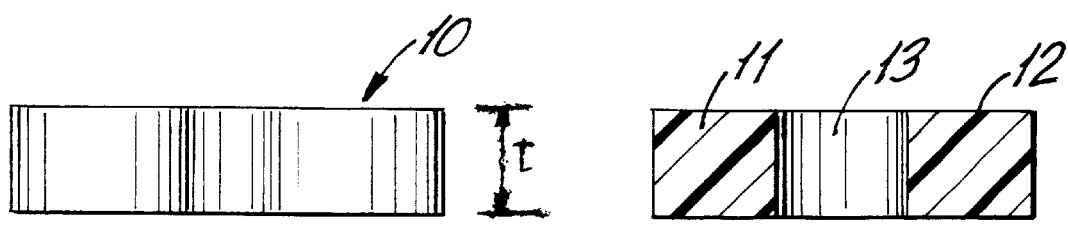
FIG. 2 is a rear face plan view of the oral protector of FIG. 1 looking in the direction of arrow F (front)
Figure 3:
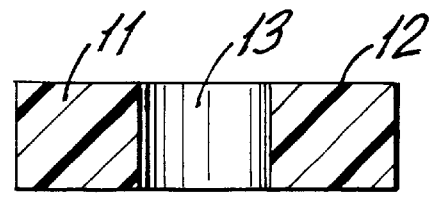
FIG. 3 is a cross-sectional view taken along line A—A of FIG. 1.
Figure 4:
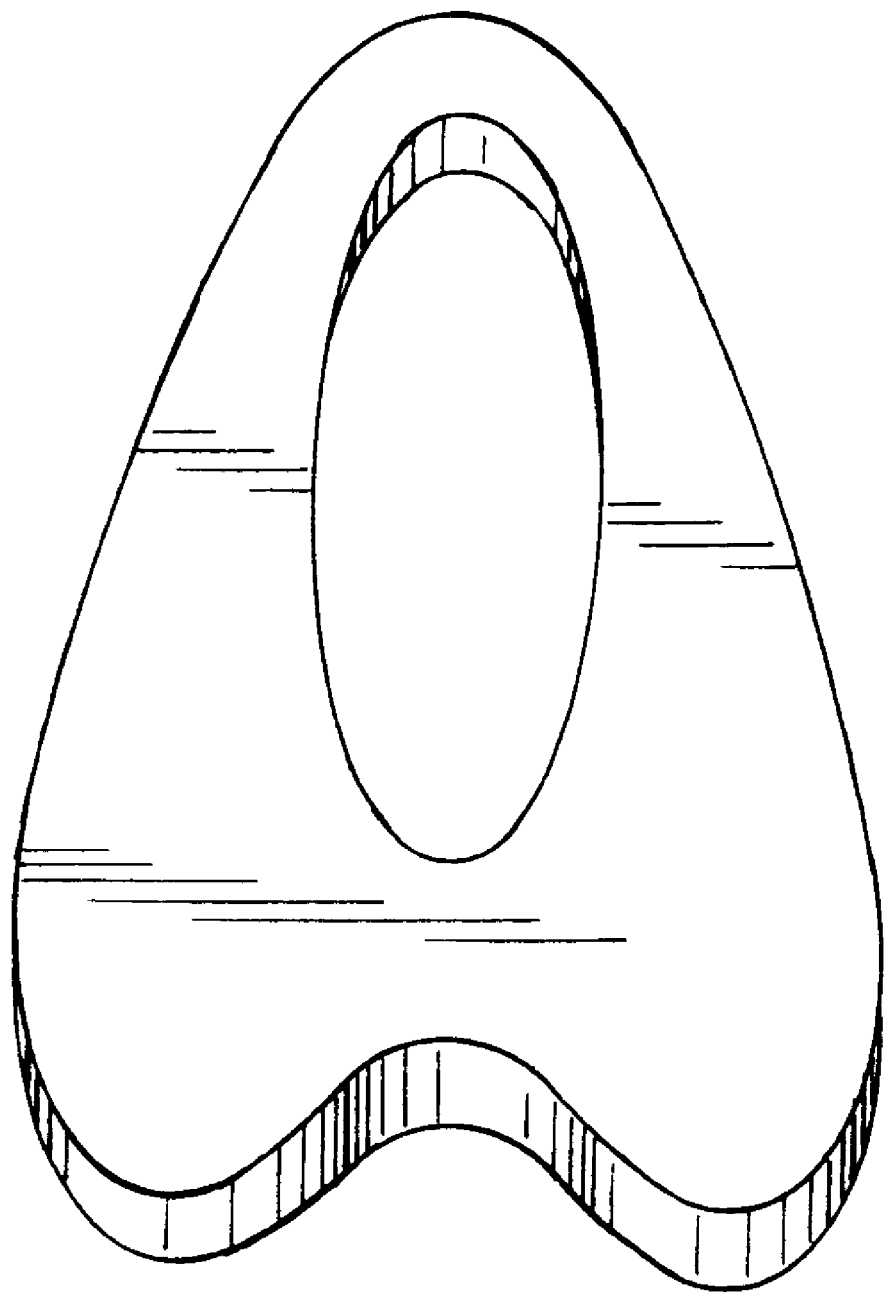
FIG. 4 is a perspective view of the oral protector of FIG. 1 looking at its rear face.

As shown in FIG. 1, the preferred width "w" of oral protector 10 is 2 3/16 inch, at its widest, and the preferred range for "w" is 1 3/4 to 2 5/8 inches. The preferred length "l" is 3 3/16 and the preferred range for "l" is 2 3/4 to 3 7/16 inches. As shown in FIG. 3, the cross-sectional view of FIG. 1 shows the two lobes 11, 12 and the elongated central opening 13. FIG. 4, shows the rear end of the device.

The thickness (dimension "t" of FIG. 2) is preferably between 3/8-inch to 5/8-inch and most preferably is 1/2-inch. Preferably the oral protector is made in two sizes, one of 3/8-inch thick and 2 3/4 inch long "l" and the other of 5/8-inch thick and 3 1/2 inch long "l".

The oral protector 10 has two rearwardly extending arms (lobes) 11,12 separated by a curved indentation 16 and an elongated central opening 13. The arms 11,12 cover the molars. The central opening 13 is preferably rounded and generally shaped like an ellipse.

The length "l2" of the opening is 2 3/4 inches, the preferred range being 2 1/4 to 3 1/4 inches. The width "w2" of the opening 13 is 1 inch, the preferred range being 3/4 to 1 1/4 inches. The top surface and bottom surface are flat and parallel to each other.

The opposite sides 14,15 are rounded, as seen in top plan view of FIG. 1. The side walls are straight, as seen in side plan view in FIG. 2.

This permits the protector to be stamped from a flat sheet of stock closed-cell foam material.

The general shape of the protector, seen in top plan view in FIG. 1, is that it has a rounded and smaller front edge 16 which leads to wider sides 14,15. The opening 13 forms an air passage and is formed along the imaginary central axis 20. The front edge 16 only extends less than 1/2-inch beyond the patient's lips and so does not interfere with an oxygen mask placed over the face during ECT.

What is claimed is:

1. An oral protector, especially adapted for use as a disposable one-usage protective device for patients during electroconvulsive therapy (ECT), comprising:
    (a) a one-piece unitary protector member composed of an elastic closed-cell foam;
    (b) said protector member being a flat member having parallel upper and lower surfaces;
    (c) said protector member having curved outer wall portions, seen in top view; and
    (d) said protector member having an imaginary central axis and an elongated central opening along said axis, said opening adapted to serve as an air passage.

2. An oral protector as in claim 1 wherein said protector member is in the range of 3/8 to 5/8 inches of thickness between said parallel surfaces.

3. An oral protector as in claim 1 wherein said protector member is stamped from a flat sheet of material.

4. An oral protector as in claim 1 wherein said protector member is formed of a plastic resin foam.

5. An oral protector as in claim 1 wherein said protector member is formed of an artificial rubber foam.

6. An oral protector as in claim 1 wherein said oral protector has a width, at its widest between said side walls, of from 1 3/4 to 2 5/8 inches.

7. An oral protector as in claim 1 wherein said oral protector has a length, at its longest, in the direction of said central axis, of from 2 1/4 to 3 1/4 inches.

8. An oral protector comprising:
    (a) a one-piece unitary protector member composed of an elastic material;
    (b) said protector member being a flat member having parallel upper and lower surfaces;
    (c) said protector member being in the range of 3/8 to 5/8 inches of thickness between said parallel surfaces;
    (d) said protector member having curved outer wall portions, seen in top view; and (e) said protector member having an imaginary central axis and an elongated central opening along said axis, said opening adapted to serve as an air passage.

9. An oral protector as in claim 8 wherein said protector member is stamped from a flat sheet of material.

10. An oral protector as in claim 8 wherein said protector member is formed of an artificial or natural non-foam rubber.

11. An oral protector comprising:
   (a) a one-piece unitary protector member composed of an elastic material;
   (b) said protector member being a flat member having parallel upper and lower surfaces;
   (c) said protector member having curved outer wall portions, seen in top view;
   (d) said protector member having an imaginary central axis and an elongated central opening along said axis, said opening adapted to serve as an air passage; and
   (e) said protector member being formed of a plastic resin closed-cell foam.

12. An oral protector comprising:
   (a) a one-piece unitary protector member composed of an elastic material;
   (b) said protector member being a flat member having parallel upper and lower surfaces;
   (c) said protector member having curved outer wall portions, seen in top view;
   (d) said protector member having an imaginary central axis and an elongated central opening along said axis, said opening adapted to serve as an air passage; and
   (e) said oral protector has a width, at its widest between said side walls, of from $1\frac{3}{4}$ to $2\frac{5}{8}$ inches.

13. An oral protector comprising:
   (a) a one-piece unitary protector member composed of an elastic material;
   (b) said protector member being a flat member having parallel upper and lower surfaces;
   (c) said protector member having curved outer wall portions, seen in top view;
   (d) said protector member having an imaginary central axis and an elongated central opening along said axis, said opening adapted to serve as an air passage; and
   (e) said oral protector having, at its longest, in the direction of said central axis, of from $2\frac{1}{4}$ to $3\frac{1}{4}$ inches.

* * * * *